United States Patent [19]

Wolfe

[11] Patent Number: 4,795,453
[45] Date of Patent: Jan. 3, 1989

[54] DOG BONE SHAPE INSERT FOR CHANNELING FLOW TO ENDS OF FEMININE NAPKIN

[75] Inventor: Dexter L. Wolfe, Appleton, Wis.

[73] Assignee: Kimberly-Clark Corporation, Neenah, Wis.

[21] Appl. No.: 123,499

[22] Filed: Nov. 20, 1987

[51] Int. Cl.$^4$ ............................................. A61F 13/16
[52] U.S. Cl. ................................................. 604/385.1
[58] Field of Search .................. 604/385.1, 385.2, 386, 604/387, 358, 370, 366

[56] References Cited

U.S. PATENT DOCUMENTS

| | | |
|---|---|---|
| 810,127 | 1/1906 | Green . |
| 2,852,026 | 9/1958 | Karr . |
| 3,291,131 | 12/1966 | Joa . |
| 3,343,543 | 9/1967 | Glassman . |
| 3,771,525 | 11/1973 | Chapuis . |
| 4,029,101 | 6/1977 | Chesky et al. . |
| 4,072,150 | 2/1978 | Glassman . |
| 4,333,465 | 6/1982 | Wiegner . |
| 4,340,058 | 7/1982 | Pierce et al. . |
| 4,410,324 | 10/1983 | Sabee ............................ 604/385.2 |
| 4,490,147 | 12/1984 | Pierce et al. ................... 604/378 |
| 4,519,800 | 5/1985 | Merry ............................ 604/385.2 |

Primary Examiner—John D. Yasko
Attorney, Agent, or Firm—Paul A. Leipold; Thomas J. Connelly

[57] ABSTRACT

The pad of the invention is comprised of a permeable cover and an impermeable backing member with an absorbent therebetween. The pad is provided with an absorbent that has at least two components. One component is a fluid transfer member that is generally in a dog bone shape. This transfer member may be formed from a generally rectangular member that has good longitudinal transfer of fluid. The generally rectangular member is provided with cuts going inward toward the center and perpendicular to each longitudinal edge at points about one-quarter of the total longitudinal length from each end. Each of these cuts extends about a third of the distance of the width of the pad forming a flap on each longer side of the rectangular planar member. The flaps are folded upward such that their ends are adjacent. This results in the formation of a dog bone shape absorbent with a thicker middle bridge portion connecting planar end pieces, placing a reservoir absorbent such as wood fluff around the insert such that the upstanding flap portion reaches to about the same height as the upper portion of the bulk absorbent. This results in a pad that presents a fluid transfer member exposed immediately below the permeable bodyside member in the longitudinal center of the pad.

20 Claims, 5 Drawing Sheets

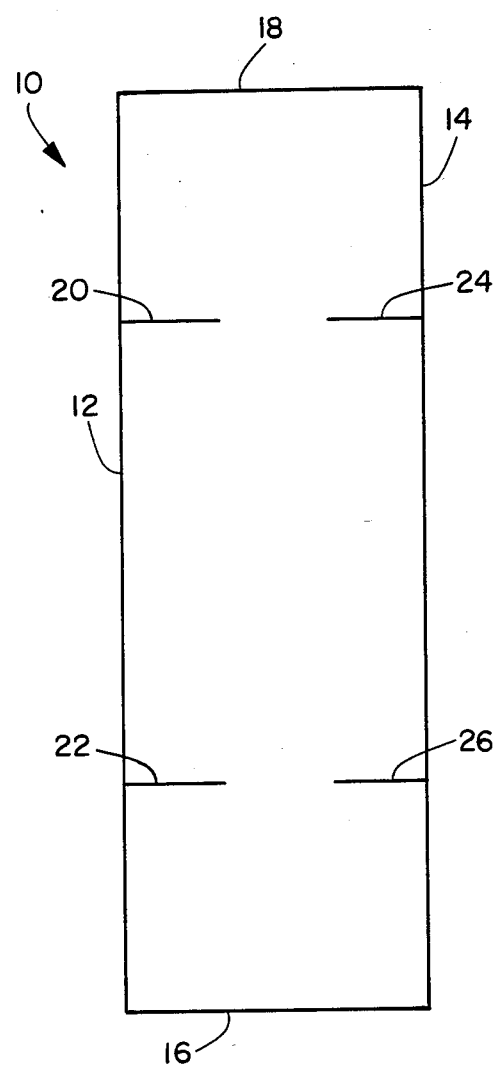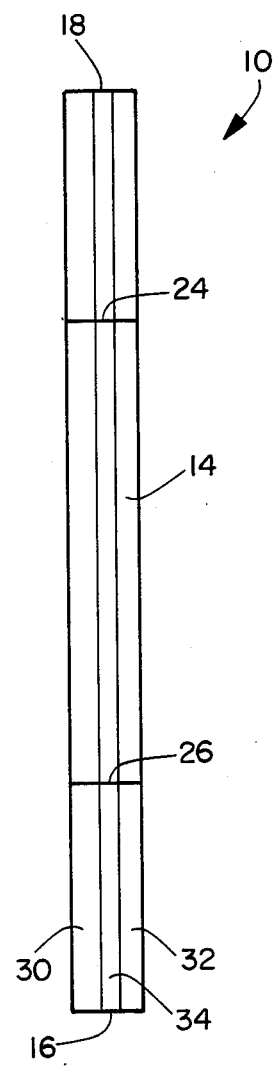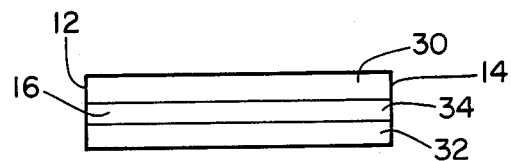
FIG. 1    FIG. 3
FIG. 2

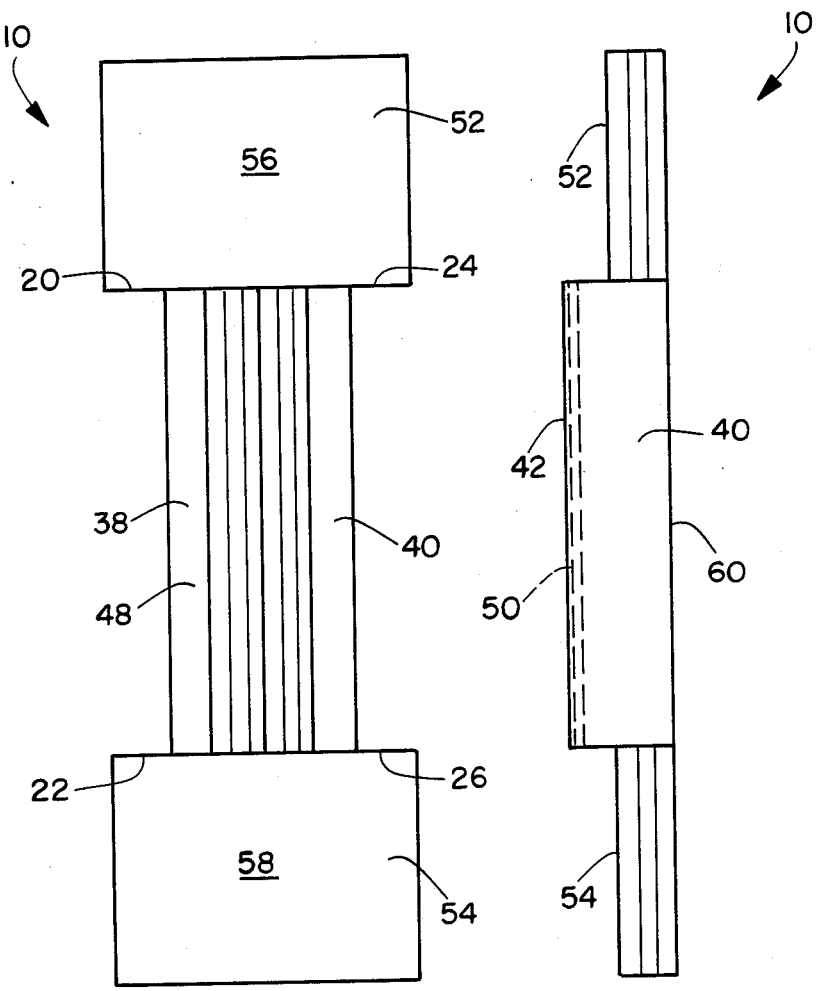
FIG. 4
FIG. 5
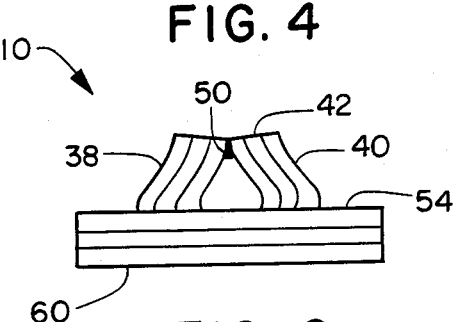
FIG. 6

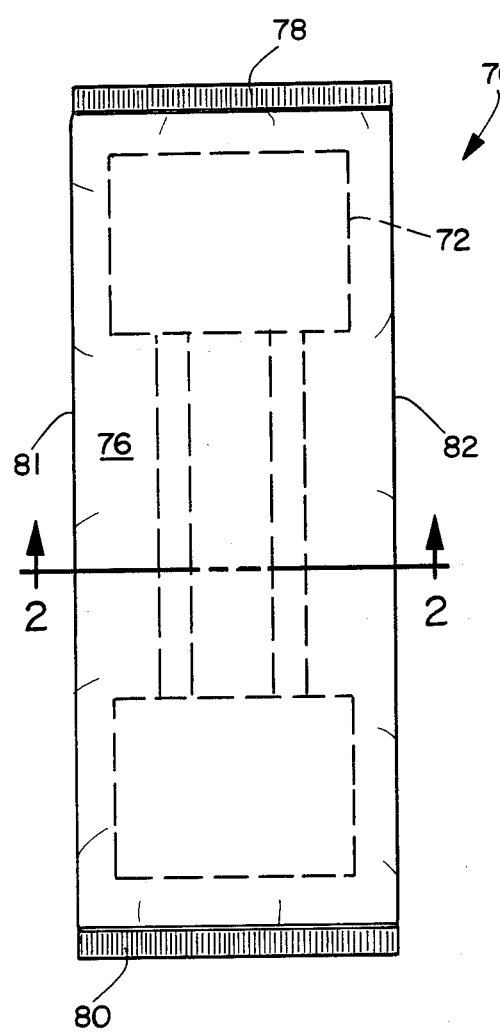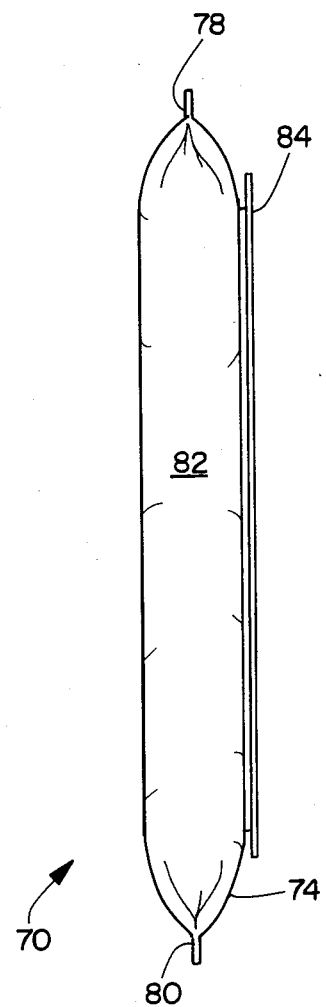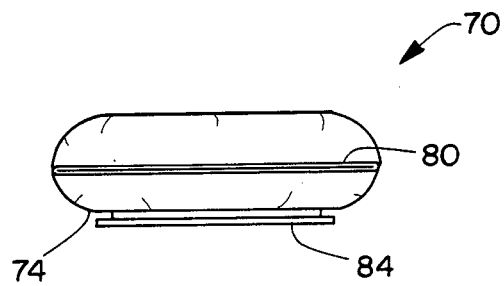
FIG. 8　　FIG. 9
FIG. 10

DOG BONE SHAPE INSERT FOR CHANNELING FLOW TO ENDS OF FEMININE NAPKIN

TECHNICAL FIELD

The present invention relates to absorbent articles and more particularly to absorbent pads for human exudate. It in particular relates to feminine care pads with a construction allowing improved distribution of fluids.

BACKGROUND OF THE ART

The present invention relates to an absorbent product, such as a sanitary napkin or incontinence product, comprising an absorbent body and a fluid-permeable layer located closest to the user when in use and a fluid-impermeable layer disposed on the opposite side—the back—of the absorbent body.

In the use of sanitary napkins there has been a problem in that the napkin is provided with much more absorbent capacity than is normally utilized by the user of the pad. The menstrual fluid tends to be distributed in the longitudinal and lateral middle of the pad. Further, the fluid in the middle section of the pad tends to be in the top or bodyside of the pad rather than in the lower portion. This concentration of the fluid in the bodyside middle portion of the pad leads to premature failure as fluid may leak over the edge of the pad or the pad may leak when it is deformed by movement of the wearer.

Attempts have been made to solve this problem by making sanitary napkins so that they more closely follow the shape of the body and have their greatest absorption capacity where the need is greatest. However, even with such pads side leakage is still a substantial problem. Further, the problem of the absorption capacity of the pad not being used because of concentration of menstrual fluids in the upper or body side of the absorbent rather than down towards the back of the absorbent remains a problem.

Another problem with conventional sanitary pads as well as incontinence pads is that if fluid is applied to the pad at a rapid rate the pad is often unable to absorb the fluid rapidly enough and the fluid will run off the sides of the pad.

It has been proposed in U.S. Pat. No. 4,333,462—Holtman that a pad having center reservoirs be formed in order to provide for receiving body fluid and its absorption. U.S. Pat. No. 4,029,101—Chesky et al. discloses a pad having an open longitudinal center slot that allows fluid to enter into the midportion of the pad. It is also disclosed in Chesky et al. that the pad may be provided with an elongated baffle to wick material laterally within the pad.

U.S. Pat. No. 2,852,026—Karowski discloses a sanitary pad in a dog bone or hourglass shape having a center portion that is thickened by cutting of flaps in a rectangular member and folding them to overlap in the center. This pad then may be wrapped with gauze and utilized as a tabbed feminine pad.

There remains a need for a pad that will make more efficient use of the absorbent available in the pad. Further, there remains a need for a pad that will better resist bending and twisting in order to maintain correct placement of the pad for delivery of exudate to the pad.

DISCLOSURE OF THE INVENTION

An object of the invention is to overcome disadvantages of prior pads for absorption of human exudate.

Another object is to provide a pad that has reduced side leakage.

An additional object is to provide an insert for pads for human exudate that will provide transfer of fluids to the ends of the pad.

A further object is to provide a feminine pad having efficient use of absorbent.

These and other objects are generally accomplished by providing a pad that is comprised of a permeable cover and an impermeable backing member with an absorbent therebetween. The pad is provided with an absorbent that has at least two components. One component is a fluid transfer member that is generally in a dog bone shape. This transfer member may be formed from a generally rectangular member that has good longitudinal transfer of fluid. The generally rectangular member is provided with cuts going inward toward the center from each longitudinal edge at points about one-quarter of the total longitudinal length from each end. Each of these cuts extends about a third of the distance of the width of the pad forming a flap on each longer side of the rectangular planar member. The flaps are folded upward such that their ends are adjacent. This results in the formation of a dog bone shape absorbent with a thicker middle bridge portion connecting planar end pieces. The pad is then formed by placing a reservoir absorbent such as wood fluff around the insert such that the upstanding flap portion reaches to about the same height as the upper portion of the bulk absorbent. The pad presents a fluid transfer member exposed immediately below the permeable bodyside member in the longitudinal center of the pad. This design results in fluids traveling down and along the fluid transfer member to the ends of the dog bone shape insert that are below the bulk absorbent. Fluids also transfer laterally from the middle bridge member to the bulk absorbent. The fluid transfer member preferably is formed of a meltblown or coform absorbent member.

BRIEF DESCRIPTION OF THE DRAWINGS

FIG. 1, FIG. 2 and FIG. 3 are views of a blank for forming the flow control member of the invention.

FIGS. 4, 5 and 6 are top, side and end views of a reinforcement member of the invention.

FIGS. 8, 9 and 10 are top, side and end views of a feminine pad utilizing the reinforcement member of the invention.

MODES FOR CARRYING OUT THE INVENTION

Figure 7:
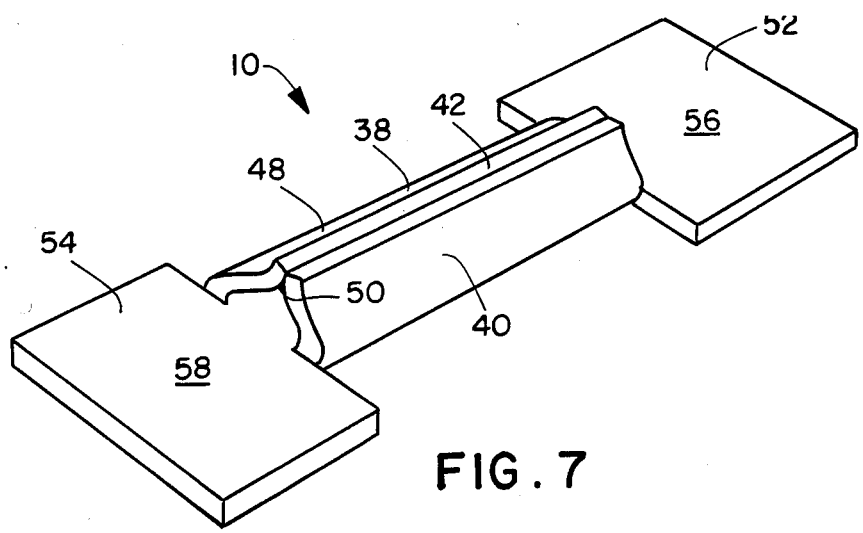
FIG. 7 is a perspective view of a reinforcement member of the invention.

The pads of the instant invention have numerous advantages over prior pads for absorption of human exudate, particularly in pads used as catamenial devices or for light feminine incontinence. The pads of the instant invention provide transport of menstrual fluids down through the pad away from the surface and to the ends of the pad and to the lower absorbent. The pads of the invention also provide a cleaner appearance as fluids transported down through the center of the pad do not spread on the surface as much. The pads further provide a visual indicator that fluids are being transferred to the ends of the pad as the centered longitudinal fluid transport member immediately below the permeable cover would be visible to the user. These and other advantages will be apparent from the description of the drawings and explanation that follows.

FIGS. 1-3 illustrate a planar blank suitable for use in formation of the fluid transfer member of the invention. Blank 10 has a generally rectangular shape with longitudinal sides 12 and 14 and ends 16 and 18. The blank as shown in FIG. 1 is provided with slits 20 and 22 on side 12 and slits 24 and 26 on side 14. The slits 20, 22, 24, and 26 are generally perpendicular to the longitudinal edges and extend about one-third of the total width of the blank 10. The preferred blank illustrated is formed of three layers. Layers 30 and 32 are of a coform material. Coform is an air-formed blend of meltblown polymer fibers and staple fibers. Preferred for the invention are blends of meltblown polypropylene and staple wood fibers. The inner layer 34 is a more dense material having smaller pores such as meltblown polypropylene.

FIG. 4 illustrates the blank 10 having the flaps 38 and 40 formed by slits 20, 22, 24 and 26 folded so that they meet to form the upper joined area 42.

FIGS. 5 and 6 are side and end views of the blank 10 after folding. The upper area 42 may be adhesively connected at area 50 where flaps 38 and 40 meet. As illustrated by FIGS. 5, 6 and 7 the flaps form a raised area 42 that extends significantly above the plane of the dog bone end unfolded portions 52 and 54. As best shown by FIG. 4 and in the perspective view of FIG. 7 the fluid transfer member has the general shape of a dog bone with the narrow bridge 48 between larger ends 52 and 54 having a greater vertical or Z-direction height than the upper surfaces 56 and 58 of the planar ends 52 and 54. However, it is noted that the lower surface 60 of the ends 52 and 54 and the lower surface of the raised middle 48 is generally planar. It is apparent that an advantage of the preferred fluid transfer member of the instant invention is that the member is three-dimensional but is easily formed from a flat sheet of fluid transfer material.

Figure 11:
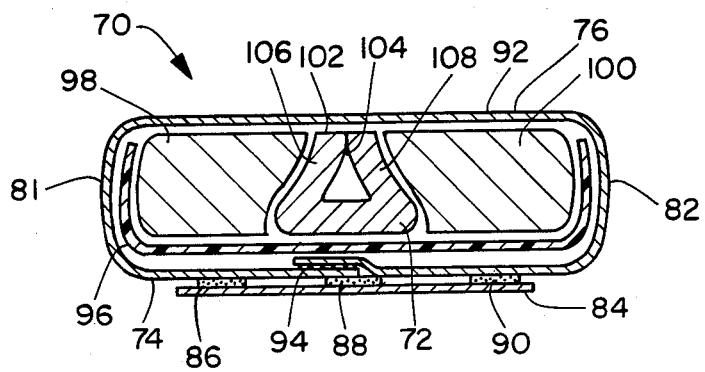
FIG. 11 is a cross-sectional view on line 2—2 of FIG. 8.

Illustrated in FIGS. 8, 9 and 10 are top, side and end views of the feminine pad 70 utilizing a reinforcement member 72 in accordance with the invention. FIG. 11 is a cross-sectional view on line 2—2 of FIG. 8. The pad 70 has a lower surface 74, upper bodyside 76, ends 78 and 80. The pad further has longitudinal sides 82 and 81. The pad has a peel strip 84 that may be removed to present garment attachment adhesive lines 86, 88 and 90. As best shown in the view of FIG. 11 the pad has a permeable bodyside cover 92 that is wrapped around the entire pad and joined at the overlapped portion by adhesive 94. The pad may also be formed by fusing the components together by heat sealing or ultrasonic sealing. The pad is provided with a liquid impermeable baffle member 96 to prevent flow of fluids from the back of the pad which would stain the wearer's garment. The pad is provided with a bulk absorbent that is divided into two portions 98 and 100 by the upraised portion 102 of the fluid transfer member 72. The upward portion is formed by adhesive connection at 104 of the flaps 106 and 108.

Figure 12:
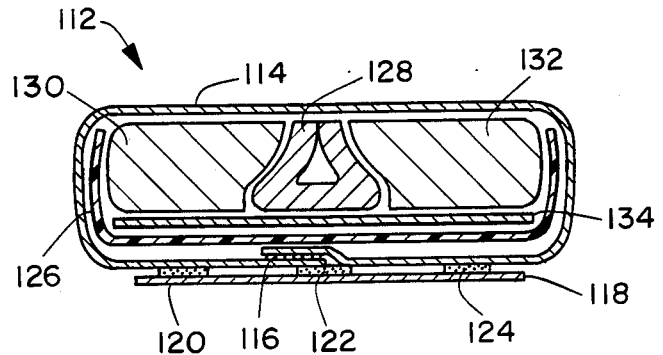
FIG. 12 is the cross-section of an alternative pad formed in accordance with the invention.

The cross-section of an alternate pad in accordance with the invention is illustrated in FIG. 12. The pad 112 has a bodyside covering permeable member 114 that is wrapped around the pad and sealed by adhesive 116. The pad in conventional manner is provided with a peel strip 118 covering garment attachment adhesive lines 120, 122 and 124. The pad further is provided with a liquid impermeable baffle 126. The fluid transfer member 128 separates bulk absorbent members 130 and 132. Member 134 is an absorbent layer that contains a superabsorbent material that will serve to store fluids such that they will not release if the pad is bent and twisted. Superabsorbents are generally hydrocolloidal materials that have the ability to absorb greater than 30 and likely 100 times their weight in fluid. They may be present either as a sheet or may be in powder that is adhered to a substrate such as tissue.

Figure 13:
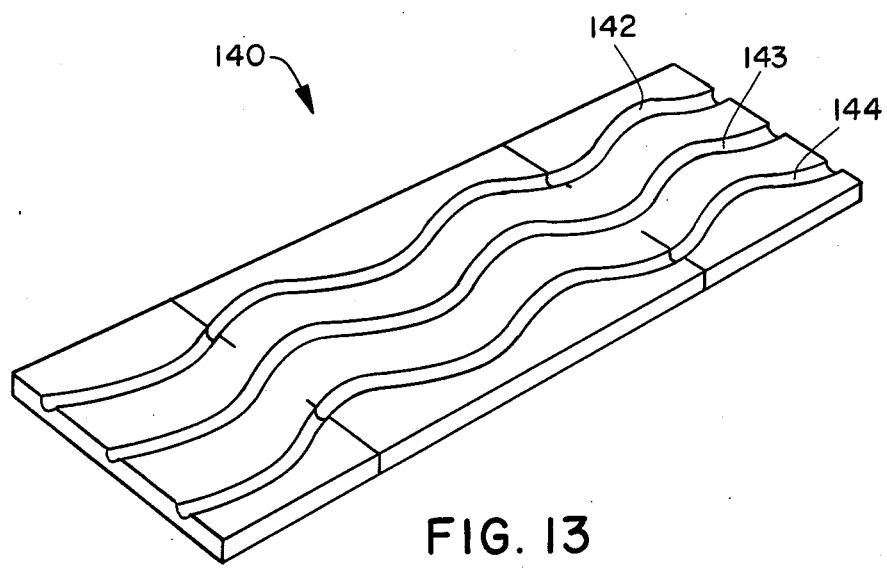
FIG. 13 is a perspective view of an embossed blank for forming the reinforcement member of the invention.
Figure 14:
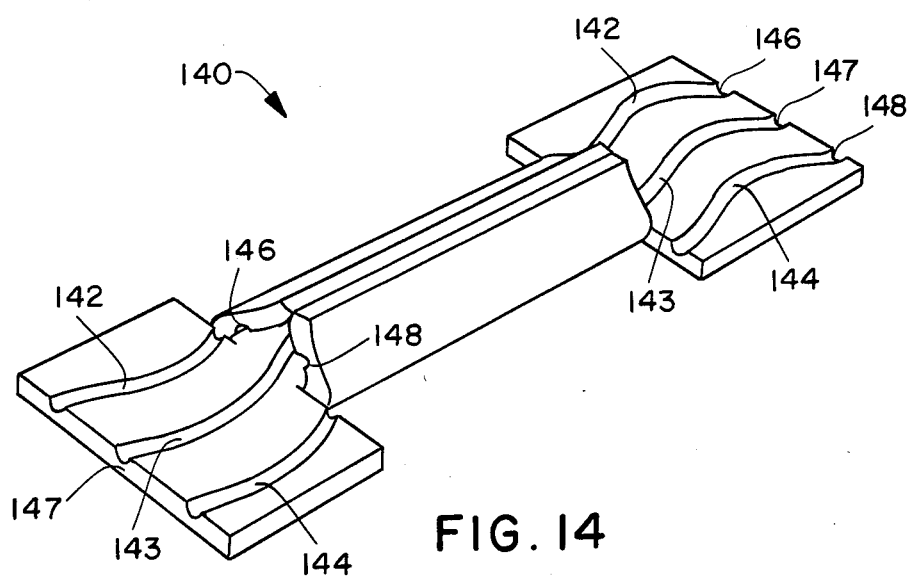
FIG. 14 is a perspective view of a reinforcing member of the invention made from the blank of FIG. 13.

Illustrated in FIGS. 13 and 14 is another embodiment of a fluid transfer member 140 in accordance with the invention. FIG. 13 is a perspective of the member prior to folding while FIG. 14 is a perspective view after the member 140 has been folded. The fluid transfer member 140 has improved longitudinal transfer characteristics as it has been provided with embossed lines 142, 143 and 144. These embossed lines create densified areas 146, 147 and 148 at the embossing lines 142, 143 and 144 respectively. These densified areas aid in longitudinal transfer of fluids as the smaller pores therein tend to transmit fluid faster by capillary action. Although shown with a generally sine-wave type pattern any suitable pattern providing longitudinal fold would be suitable. Further it is possible that a crosshatch pattern could be utilized in order to provide faster fluid flow in both directions of the fluid transfer members.

The fluid transfer material may be any material that will readily transfer fluids as well as give up fluids to absorbents such as wood fluff. These materials generally have a hydrophilic and a hydrophobic component. Suitable materials are bonded carded webs, coform and meltblown materials. Coform is an air-formed blend of meltblown polymer and staple fibers. The preferred coform is a meltblown polypropylene and devillicated wood fibers.

Other preferred materials are ultrasonically bonded carded webs that are blends of polypropylene, polyester and rayon. Another preferred material is macrofiber coform which may be defined as coform that has a fiber diameter of greater than about 15 microns diameter. Another preferred material is a bonded carded web of a blend of polyester and rayon. As illustrated in the drawings a composite structure such as the illustrated layered structure of coform and meltblown material is another preferred material. The transfer material should have a hydrophilic component to facilitate the flow of fluids within the transfer layer. However it should also include a hydrophobic component in order that fluids will preferentially transfer to other absorbents such as wood fluff that are more uniformly hydrophilic. Further, it is possible that some of all of the fibers forming the transfer members may be treated prior to or during formation of the carded web or coform in order to make them hydrophilic or hydrophobic as the case may be. It is possible that the coform materials may be blends of staple fibers such as rayon as well as wood in combination with the air-formed polypropylene or other polymer fibers.

The material selected as the reservoir or bulk absorbent that absorbs the fluids from the transfer members in the invention products may be any material that will preferentially absorb fluids from the transfer layers. Further such materials should not preferentially cause flow of liquid from the reservoir absorbent back to the transfer material and therefore may be any absorbent with good liquid holding ability and the ability to preferentially absorb fluids from the transfer member. Typical of such materials are cellulose sponge, polymer sponge, tissue and rayon fibers. The preferred material is wood fluff as it has high liquid holding ability and low cost. It is also possible that superabsorbents may be added to the bulk absorbent in order to better hold fluid. Superabsorbents are hydrogel materials that have the ability to hold greater than 30 times and preferably 100 times their weight of fluid.

The invention has the advantage that the Z-direction transfer is improved such that fluids are quickly and efficiently moved from the top surface of the pad below the cover and to the bulk absorbent at the sides of the middle of the pad and to the ends of the pad. The bulk absorbent then is able to preferentially absorb fluids from the transfer member. The pads further have the advantage that by having the open area in the middle between bulk absorbents on each side the pad tends to flex in the middle and is better able to conform to the body. As it flexes with the middle portion lifting upward for better contact with the labia, the fluid transfer member then is better exposed to initial contact with the fluid as it leaves the body of the wearer. The pads of the invention generally do not require a tissue wrapping member around the fluff absorbents. The use of the liquid transfer member provides sufficient strength that the tissue wrap of the fluff is not necessary. This is a cost savings in that the wrap is not necessary.

The following examples are intended to be illustrative and not exhaustive in setting out the invention.

EXAMPLE

A fluid transfer insert is prepared by forming a three-layered laminate about 6 inches long and about 2 inches wide. The top and bottom layers are 135 grams per square meter coform (70% wood pulp and 30% polypropylene) and the center layer is polypropylene microfiber of about 90 grams per square meter. The laminate is embossed lengthwise with a sinusoidal pattern such as utilized in the KOTEX® LIGHTDAYS® feminine pad. A triangular projection is formed in the central 3-inch insert by cutting flaps about ⅜ inch in from the edges and folding the central edges up in the central portion as shown in FIGS. 4–6 of the specification. The folded-up edges are fusibly tacked together utilizing hotmelt adhesive. The triangular projection is then inserted into a 3-inch long slit in a fluff layer of approximately 450 grams per square meter so that the top of the triangular is about at the upper portion of the fluff. The planar end pieces rest upon the ends of the fluff that has a size of generally about 6 inches by about 3 inches wide. The pad is then formed by covering the upper surface where the triangular projection is through the fluff with a conventional spunbond feminine care cover material. This cover material extends beyond the fluff and is adhesively connected to a polypropylene film backing material at the edges. This material when tested as a feminine pad provides good transfer of fluids from the central middle portion to the ends and the lower portion of the fluff.

While the invention has been illustrated with feminine care pads, the invention also may find utility in other areas such as diapers or bandages. Further, while shown utilized in a generally rectangular planar feminine pad, the liquid transfer system of the invention would find utility in other types of feminine pads including pads designed for partial labial disposition disclosed in U.S. Pat. No. 4,631,062—Lassen et al. or elasticized pads such as illustrated in U.S. Pat. No. 4,668,230—Damico et al.

The impermeable backing member may be any suitable liquid impermeable material such as films of polypropylene or polyethylene. The impermeable backing material also may be a vapor permeable material such as some meltblown materials or GORETEX® type materials. The permeable bodyside member may be any suitable known bodyside material. Typical of such materials are perforated films and spunbond. A preferred material is a spunbond polypropylene as it is low in cost and effective.

While the dog bone shape fluid transfer member of the invention has been shown as formed from a generally rectangular planar member, it also could be formed with rounded outer corners rather than the square corners illustrated. Further, the fluid transfer member could be formed with the cut lines to form the flaps being curved rather than straight or angled at other than 90° from the edge of the liquid transfer member. However, it is desirable that the lines in any case extend from each side in about one-third of the total distance across the fluid transfer member. It is also possible to form the liquid transfer member of a contrasting color to the color of the other bulk absorbent in order to highlight its presence to the pad user. These and other variations are intended to be included by the scope of the claims attached hereto.

I claim:

1. A pad for absorption of human exudate comprising a bodyside permeable member, a liquid impermeable backing member and an absorbent between said cover and said backing member wherein said absorbent comprises a reservoir absorbent and a dog bone shape fluid transfer absorbent, said dog bone shape absorbent comprising planar end pieces and a bridging portion of said dog bone that extends between said planar end pieces and is thicker than said planar end pieces of said dog bone shape fluid transfer absorbent and wherein said bridging portion extends in said pad from adjacent said backing member upward to an area immediately below said permeable member.

2. The pad of claim 1 wherein said fluid transfer absorbent is thicker in the narrow portion of said dog bone shape absorbent so as to extend to said area immediately below said cover.

3. The pad of claim 1 wherein said fluid transfer member is embossed.

4. The pad of claim 2 wherein said fluid transfer member comprises a generally rectangular member that has two flaps folded together to form said thicker portion.

5. The pad of claim 1 wherein the ends of said dog bone shape fluid transfer absorbent extends between said reservoir absorbent and said liquid impermeable backing and said bridge portion of said dog bone absorbent extends between said impermeable backing and said permeable member.

6. The pad of claim 5 wherein said fluid transfer member preferentially transfers fluid from said transfer member to said reservoir absorbent.

7. The pad of claim 5 wherein said fluid transfer member comprises a laminate of meltblown polymer and coform.

8. The pad of claim 5 wherein said bridge portion extending through said reservoir absorbent comprises folds of said fluid transfer absorbent.

9. The pad of claim 5 wherein said fluid transfer member is formed by folding a generally rectangular planar sheet.

10. A fluid transfer member for a pad for absorption of human exudate comprising a generally planar fibrous member having two enlarged portions separated by a narrower thicker portion.

11. The member of claim 10 comprising meltblown fibers.

12. The member of claim 10 further comprising longitudinal embossed areas.

13. A method of forming a fluid transfer member for a pad for absorption of human exudate comprising providing a planar rectangular fibrous absorbent having longitudinal edges longer than the ends of said pad, cutting at two locations on each of the longitudinal edges about one-third of the distance to the longitudinal center of said absorbent, and folding the center portions of each longitudinal edge toward each other until they meet forming an upraised area.

14. The method of claim 13 further comprising adhesively connecting said center portions where they meet.

15. A method of forming a pad for absorption of human exudate comprising providing a planar rectangular fibrous liquid transfer absorbent having longitudinal edges longer than the ends of said pad, cutting at two locations on each of the longitudinal edges about one-third of the distance to the longitudinal center line of said absorbent, and folding the center portions of each longitudinal edge toward each other until they meet, adhesively connecting said center portions where they meet to form an upraised center portion, placing a bulk absorbent overlaying all of said liquid transfer absorbent excepting the upraised center portions.

16. The method of claim 15 further comprising providing a liquid permeable web adjacent said bulk absorbent and said center portion an impermeable member underlying said pad on the side opposing said permeable member.

17. The pad of claim 1 wherein said reservoir absorbent comprises wood fluff.

18. The pad of claim 1 wherein said dog bone shape fluid transfer absorbent comprises coform.

19. The pad of claim 1 wherein said fluid transfer absorbent comprises a carded web.

20. The pad of claim 1 wherein said fluid transfer member comprises a hydrophobic component and a hydrophilic component.

* * * * *

UNITED STATES PATENT AND TRADEMARK OFFICE
CERTIFICATE OF CORRECTION

PATENT NO. : 4,795,453

DATED : January 3, 1989

INVENTOR(S) : Dexter L. Wolfe

It is certified that error appears in the above-identified patent and that said Letters Patent is hereby corrected as shown below:

IN THE CLAIMS:

Claim 16, Column 8, line 17, after the word "portion" insert --and--.

Signed and Sealed this

Twenty-first Day of November, 1989

Attest:

JEFFREY M. SAMUELS

*Attesting Officer*    *Acting Commissioner of Patents and Trademarks*